United States Patent [19]

Stockinger et al.

[11] 4,326,069
[45] Apr. 20, 1982

[54] N-SUBSTITUTED ASPARTIC ACID MONOESTERS

[75] Inventors: Friedrich Stockinger, Hölstein; Sameer H. Eldin, Birsfelden; Friedrich Lohse, Oberwil, all of Switzerland

[73] Assignee: Ciba-Geigy Corporation, Ardsley, N.Y.

[21] Appl. No.: 144,136

[22] Filed: Apr. 28, 1980

[30] Foreign Application Priority Data

May 8, 1979 [CH] Switzerland ............... 4306/79

[51] Int. Cl.³ ............... C07C 101/22; C07D 233/61
[52] U.S. Cl. ...................... 560/169; 546/232; 546/246; 548/341; 560/145
[58] Field of Search ............ 560/169; 546/329, 232; 548/342, 341

[56] References Cited

U.S. PATENT DOCUMENTS 3,182,064  5/1965  Shapiro et al. ............ 546/329 X
3,979,442  9/1976  Schafer et al. ............ 560/169 X
4,284,755  8/1981  Lohse et al. ............... 560/169 X

FOREIGN PATENT DOCUMENTS 1561451  2/1969  France ...................... 560/169
1050678  12/1966  United Kingdom .

OTHER PUBLICATIONS

Saunders, T., et al., J. Poly. Sci., A-1, 5, 1609, (1967).
Laliberte, R., et al., Can. J. Chem., 40, 163 (1962).
Bert et al., Chem. Abst., vol. 74, abst. 23825q, (1971).
Liu et al., Chem. Abst. vol. 83, abst. 179534r, (1975).
Karten et al., J. Med. Chem., vol. 9, pp. 447–448, (1966).
Schaefer et al, Chem. Abst., vol. 81, abst. 51065c, (1974).
Zilkha et al., J. Org. Chem., vol. 24, pp. 1096 to 1098, (1959).

Primary Examiner—Richard A. Schwartz
Attorney, Agent, or Firm—Luther A. R. Hall

[57] ABSTRACT

N-substituted aspartic acid monoesters of the formula I

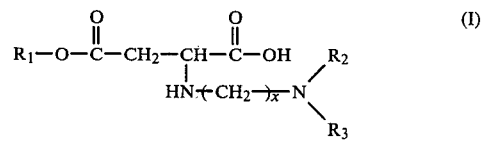

wherein for example $R_1$ is an alkyl group having 1 to 12 C atoms, cyclohexyl, phenyl, tolyl or benzyl, x is 2 or 3, $R_2$ and $R_3$ are each a methyl or ethyl group, or together with the N atom they form an N-heterocyclic ring, are obtained by adding, by means of an addition reaction, to 1 mol of a maleic acid monoester of the formula II

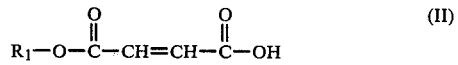

1 mol of an amine of the formula III

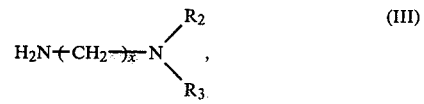

in the presence of a tertiary amine. The novel N-substituted aspartic acid monoesters are valuable curing accelerators for epoxide resin mixtures containing dicyandiamide or a polycarboxylic acid anhydride as curing agent. They are also suitable alone as catalytically acting curing agents for epoxide resins.

6 Claims, No Drawings

N-SUBSTITUTED ASPARTIC ACID MONOESTERS

The present invention relates to N-substituted aspartic acid monoesters, to processes for producing them, and to their use as accelerators in the curing of epoxide resins, or as latent curing agents for epoxide resins.

It is known that in the curing of epoxide resins with polycarboxylic acid anhydrides or with dicyandiamide there are added to the curable mixtures curing accelerators, for example tertiary amines. As is evident from the G.B. Pat. No. 1,050,678, additions of tertiary amines, such as benzyldimethylamine, effect in the curing of epoxide resins with polycarboxylic acid anhydrides a shortening of the curing time but no lowering of the relatively high curing temperatures. Furthermore, the properties of the cured epoxide resins are impaired by the use of tertiary amines as accelerators. In order to counteract these disadvantages, there is suggested in the G.B. Pat. No. 1,050,678 the use of imidazoles as curing accelerators for the anhydride curing of epoxide resins. In comparison with other known accelerators, imidazoles are very effective accelerators; however, imidazole-containing, one-component systems formed from epoxide resins and polycarboxylic acid anhydrides, such as moulding materials or sintering powders, have the disadvantage of inadequate storage stability.

The same disadvantages are associated with the curing of epoxide resins with dicyandiamide in the presence of tertiary amines as curing accelerators, which curing method is known from "Journal of Polymer Science", section A-1, Vol. 5, pp. 1609–1617 (1967). The customary accelerating additions of tertiary amines, which result in a considerable acceleration of gelling and curing when epoxide resins are cured with polycarboxylic acid anhydrides, effect only a slight acceleration when dicyandiamide is used as the curing agent. By the addition of larger amounts of accelerator the curing time can probably be shortened, but the storage stability of the epoxide resin/dicyandiamide mixtures is largely or completely lost. In most cases, however, dicyandiamide is employed as curing agent for epoxide resins just on account of the good storage stability of the curable epoxide resin mixtures.

It has now been found that N-substituted aspartic acid monoesters are valuable curing accelerators for the curing of epoxide resins both with polycarboxylic acid anhydrides and with dicyandiamide, because in one-component systems these monoesters do not lead to the disadvantage described above with regard to unfavourable storage stability.

The present invention thus relates to novel N-substituted aspartic acid monoesters of the formula I

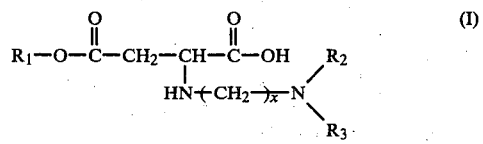

wherein $R_1$ is an alkyl group which has 1 to 12 C atoms and which optionally contains ether oxygen atoms, or it is cyclohexyl, phenyl, tolyl or benzyl, x is the number 2 or 3, $R_2$ and $R_3$ independently of one another are each methyl or ethyl, or together with the N atom they form an N-heterocyclic ring of the formula

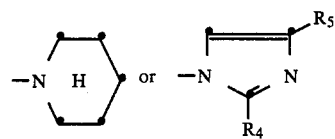

wherein $R_4$ and $R_5$ independently of one another are each a hydrogen atom, methyl or ethyl.

Preferably, in the formula I, $R_1$ is an alkyl group having 1 to 6 C atoms or a cyclohexyl group, x is the number 3, and $R_2$ and $R_3$ are each a methyl or ethyl group, especially they are each a methyl group, or together with the N atom they form an N-heterocyclic ring of the formula

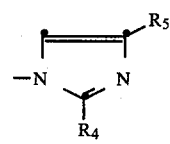

wherein $R_4$ is methyl, and $R_5$ is a hydrogen atom or ethyl, particularly a hydrogen atom.

$R_1$ as alkyl can have for example the following meanings:

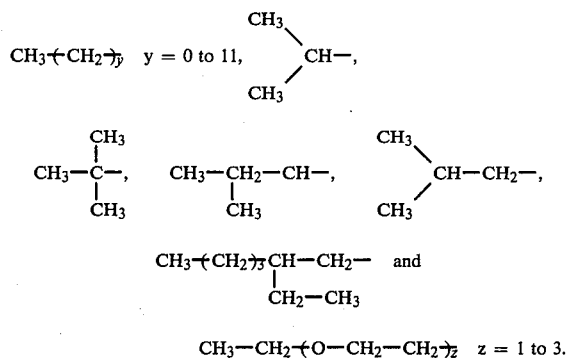

$$CH_3-CH_2-(O-CH_2-CH_2)_{\overline{z}} \quad z = 1 \text{ to } 3.$$

The N-substituted aspartic acid monoesters of the formula I can be produced, using the processes described in "Journal of Organic Chemistry", Vol. 24 (1959), pp. 1096–98, and in "Canadian Journal of Chemistry", Vol. 40 (1962), pp. 163–5, by adding, by means of an addition reaction, to 1 mol of a maleic acid monoester of the formula II

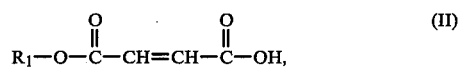

wherein $R_1$ has the same meaning as in the formula I, 1 mol of an amine of the formula III

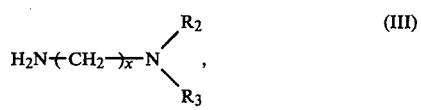

wherein $R_2$, $R_3$ and x have the same meanings as in the formula I, in the presence of a tertiary amine.

A compound of the formula I according to the invention is preferably produced by starting with a maleic acid monoester of the formula II wherein $R_1$ is an alkyl group having 1 to 6 C atoms or a cyclohexyl group, and reacting this maleic acid monoester preferably with an amine of the formula III wherein $R_2$ and $R_3$ are each a methyl or ethyl group, or together with the N atoms they form an N-heterocyclic ring of the formula

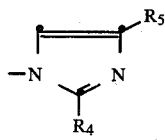

wherein $R_4$ is methyl, and $R_5$ is a hydrogen atom or ethyl, and x is 3, in the presence of triethylamine or pyridine, particularly triethylamine.

The maleic acid monoesters of the formula II are known (cp. for example Canadian Journal of Chemistry, Volume 40 (1962), pp. 163–165. The amines of the formula III are likewise known compounds.

As mentioned hereinbefore, the aspartic acid derivatives according to the invention are valuable curing accelerators for the curing of epoxide resins with polycarboxylic acid anhydrides or with dicyandiamide. The aspartic acid derivatives according to the invention are also suitable as catalytic curing agents for epoxide resins. The curable epoxide resin mixtures containing the aspartic acid derivatives according to the invention are distinguished by their excellent storage stability at room temperature, and they have a greatly improved latency factor compared with that of epoxide resin mixtures containing known curing accelerators. By latency factor is meant the quotient of gelling time at lower temperature over gelling time at higher temperature:

$$\left(\text{latency factor} = \frac{\text{gelling time at lower temperature}}{\text{gelling time at higher temperature}}\right)$$

the choice of the higher temperature being optional but generally corresponding to processing temperatures of the curable epoxide resin mixture.

The present invention relates therefore also to the use of the aspartic acid monoesters of the formula I as curing accelerators or catalytically acting curing agents for epoxide resins.

In the curing of epoxide resins with polycarboxylic acid anhydrides, the curing accelerators according to the invention are used in amounts of 0.5 to 2 percent by weight, preferably 1 to 1.5 percent by weight, relative to the weight of epoxide resin.

As curing accelerators in the curing of epoxide resins with dicyandiamide, the aspartic acid derivatives according to the invention are used in amounts of 0.1 to 1.0 percent by weight, preferably 0.3 to 0.5 percent by weight, relative to the proportion of epoxide resin.

For the catalytic curing of epoxide resins, the aspartic acid derivatives according to the invention are used in amounts of 2 to 10 percent by weight, preferably 3.5 to 6 percent by weight, relative to the proportion of epoxide resin.

All known classes of epoxide resins are suitable as epoxide resins for the curing of which the aspartic acid derivatives according to the invention can be used as curing accelerators. Especially suitable are epoxide compounds having on average more than one glycidyl group, β-methylglycidyl group or 2,3-epoxycyclopentyl group, each bound to a hetero atom (for example sulfur, preferably oxygen or nitrogen); there may be mentioned in particular: bis-(2,3-epoxycyclopentyl)-ether; di- or polyglycidyl ethers of polyhydric aliphatic alcohols, such as 1,4-butanediol, or polyalkylene glycols, such as polypropylene glycols; di- or polyglycidyl ethers of cycloaliphatic polyols, such as 2,2-bis-(4-hydroxycyclohexyl)-propane; di- or polyglycidyl ethers of polyvalent phenols, such as resorcin, bis-(p-hydroxyphenyl)-methane, 2,2-bis-(p-hydroxyphenyl)-propane (=diomethane), 2,2-bis-(4'-hydroxy-3',5'-dibromophenyl)-propane, 1,1,2,2-tetrakis-(p-hydroxyphenyl)-ethane, or condensation products of phenols with formaldehyde, obtained under acid conditions, such as phenol-novolaks and cresol-novolaks; di- or poly-(β-methylglycidyl)-ethers of the above-mentioned polyhydric alcohols or polyvalent phenols; polyglycidyl esters of polyvalent carboxylic acids, such as phthalic acid, terephthalic acid, $\Delta^4$-tetrahydrophthalic acid and hexahydrophthalic acid; N-glycidyl derivatives of amines, amides and heterocyclic nitrogen bases, such as N,N-diglycidylaniline, N,N-diglycidyltoluidine, N,N,N',N'-tetraglycidyl-bis-(p-aminophenyl)-methane; triglycidylisocyanurate; N,N'-diglycidylethylene-urea; N,N'-diglycidyl-5,5-dimethylhydantoin, N,N'-diglycidyl-5-isopropylhydantoin; N,N'-diglycidyl-5,5-dimethyl-6-isopropyl-5,6-dihydantoin; and N,N'-diglycidyl-5,5-dimethyl-6-isopropyl-5,6-dihydrouracil.

Suitable epoxide compounds are also alicyclic diepoxides, such as limonenedioxide, dicyclopentadienedioxide, ethylene glycol-bis-(3,4-epoxytetrahydrocyclopentadien-8-yl)-glycidyl ethers, as well as compounds having two epoxycyclohexyl radicals, such as diethylene glycol-bis-(3,4-epoxycyclohexanecarboxylate), bis-3,4-(epoxycyclohexylmethyl)-succinate, 3',4'-epoxy-6'-methylcyclohexylmethyl-3,4-epoxy-6-methylcyclohexane-carboxylate and 3',4'-epoxyhexahydrobenzal-3,4-epoxycyclohexane-1,1-dimethanol.

The following may be mentioned as examples of suitable polycarboxylic acid anhydrides which can be used together with the curing accelerators according to the invention for curing epoxide resins: cycloaliphatic polycarboxylic acid anhydrides, such as tetrahydrophthalic acid anhydride, methyltetrahydrophthalic acid anhydride, hexahydrophthalic acid anhydride, methylhexahydrophthalic acid anhydride, endomethylenetetrahydrophthalic acid anhydride, methylendomethylene-tetrahydrophthalic acid anhydride (=methylnadicanhydride), the Diels-Alder adduct formed from 2 mols of maleic acid anhydride and 1 mol of 1,4-bis-(cyclopentadienyl)-2-butene, the eutectic mixtures of these polycarboxylic acid anhydrides, as well as isomeric mixtures of the methyl-substituted tetrahydrophthalic acid anhydrides, or specific aromatic polycarboxylic acid anhydrides, such as trimellitic acid anhydride or pyromellitic acid anhydride.

In the following Examples, the term 'parts' denotes parts by weight and, except where otherwise stated, percentages are percent by weight.

EXAMPLE 1

N-(3'-Dimethylaminopropyl)-aspartic acid-4-methyl ester 286 g (2.0 mols+10% excess) of maleic acid-monomethyl ester are placed into a glass flask fitted with a blade stirrer, thermometer, reflux condenser and dropping funnel, and, with ice-water cooling, 400 ml of triethylamine are added dropwise at 6°–11° C. internal temperature within 1 hour and 35 minutes. The cooling is subsequently removed, 204 g (2.0 mols) of 3-dimethylaminopropylamine are quickly added, and the mixture is reacted for 10 minutes at 87°–90° C. and is then cooled to room temperature; the crystalline crude product is mixed with 1 liter of acetone, the suspension is filtered, and the filter residue is washed with acetone. The yield after drying at 80° C. in vacuo is 296 g (63.7% of theory) of a crystalline aspartic acid derivative, which melts at 171°–172° C.

Elementary analysis:

| calculated | found |
|---|---|
| 51.71% C | 51.66% C |
| 8.68% H | 8.67% H |
| 12.06% N | 12.32% N. |

The 100 MHz-$^1$H-NMR spectrum and mass spectrum agree with the following structure:

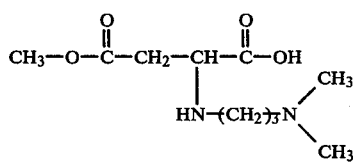

EXAMPLE 2

N-(3'-Dimethylaminopropyl)-aspartic acid-4-ethyl ester

In a manner analogous to that of Example 1, 360.3 g (2.5 mols) of maleic acid monoethyl ester are placed into the glass flask and, with cooling, 500 ml of triethylamine are added dropwise. 306.5 g (2.5 mols+20% excess) of 3-dimethylaminopropylamine are subsequently added, and the reaction mixture is reacted at 64°–90° C. for 50 minutes. The crude product is processed according to Example 1, and the yield is 568.2 g (92.3% of theory) of a white crystalline aspartic acid derivative having a melting point of 168°–169° C.

Elementary analysis

| calculated | found |
|---|---|
| 53.64% C | 53.44% C |
| 9.00% H | 9.02% H |
| 11.37% N | 11.53% N. |

The 100 MHz-$^1$H-NMR spectrum is in agreement with the following structure:

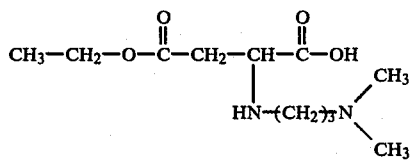

EXAMPLE 3

N-(3'-Dimethylaminopropyl)-aspartic acid-4-n-butyl ester

In the apparatus described in Example 1, 500 ml of triethylamine are added with cooling, within 2 hours and 35 minutes, at 4°–10° C. internal temperature to 430.5 g (2.5 mols) of maleic acid-mono-n-butyl ester. There are subsequently quickly added 306.5 g (2.5 mols+20% excess) of 3-dimethylaminopropylamine, and the mixture is reacted for 30 minutes at 90°–95° C. The reaction product is processed in a manner analogous to that described in Example 1 to obtain a yield of 595 g (86.8% of theory) of a crystalline aspartic acid derivative, which melts at 154°–157.5° C.

Elementary analysis

| calculated | found |
|---|---|
| 56.65% C | 56.62% C |
| 9.51% H | 9.65% H |
| 10.16% N | 10.69% N |
| 0.46% H$_2$O | 0.46% H$_2$O. |

The 100 MHz-$^1$-NMR spectrum is in agreement with the following structure:

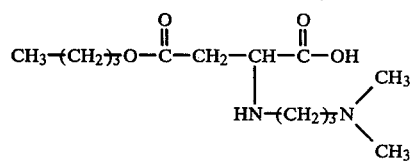

EXAMPLE 4

N-(3'-Dimethylaminopropyl)-aspartic acid-4-isopropyl ester 395.2 g (2.5 mols) of maleic acid-monoisopropyl ester, 500 ml of triethylamine and 306.5 g (2.5 mols+20% excess) of 3-dimethylaminopropylamine are reacted according to Example 1, and the reaction product is subsequently purified to yield 616.4 g (94.7% of theory) of a white crystalline aspartic acid derivative of which the melting point is 163.5°–165.5° C.

Elementary analysis

| calculated | found |
|---|---|
| 55.12% C | 55.12% C |
| 9.32% H | 9.13% H |
| 10.71% N | 11.00% N |
| 0.45% H$_2$O | 0.45% H$_2$O. |

The 100 MHz-$^1$H-NMR spectrum is in agreement with the following structure

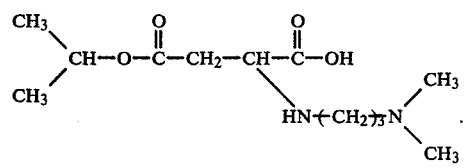

EXAMPLE 5

N-(3'-Dimethylaminopropyl)-aspartic acid-4-cyclohexyl ester

In a manner analogous to that described in Example 1, 100 ml of triethylamine are added dropwise, with cooling, to 99.1 g (0.5 mol) of maleic acid-monocyclohexyl ester, and the mixture is reacted with 61.3 g (0.5 mol+20% excess) of 3-dimethylaminopropylamine for 1 hour at 80°–93° C. The reaction product is purified as described in Example 1 to yield 109.9 g (73.2% of theory) of the desired aspartic acid derivative having a melting point of 150°–152.5° C.

Elementary analysis

| calculated | found |
| --- | --- |
| 59.98% C | 60.10% C |
| 9.40% H | 9.50% H |
| 9.33% N | 9.62% N. |

The 100 MHz-$^1$H-NMR spectrum is in agreement with the following structure:

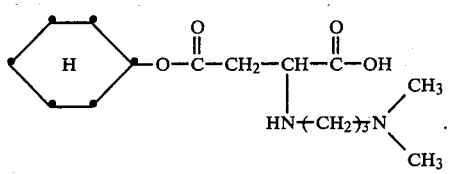

EXAMPLE 6

N-(3'-Methylethylaminopropyl)-aspartic acid-4-cyclohexyl ester 43.6 g (0.2 mol+10% excess) of maleic acid-monocyclohexyl ester, 40 ml of triethylamine and 23.2 g (0.2 mol) of 3-(methylethylamino)-propylamine are reacted in the manner described in Example 1 and analogously further processed. The yield is 36.3 g (57.7% of theory) of a crystalline aspartic acid derivative which, after recrystallisation in acetone, melts at 123.5°–127.5° C.

Elementary analysis

| calculated | found |
| --- | --- |
| 60.56% C | 60.36% C |
| 9.53% H | 9.67% H |
| 8.83% N | 8.88% N |
| 0.092% H$_2$O | 0.92% H$_2$O. |

The 100 MHz-$^1$H-NMR spectrum is in agreement with the following structure:

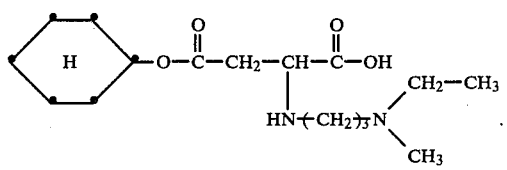

EXAMPLE 7

N-(3'-Diethylaminopropyl)-aspartic acid-4-methyl ester 71.5 g (0.5 mol+10% excess) of maleic acid-monomethyl ester are reacted, in the manner described in Example 1, with 100 ml of triethylamine and 65.1 g (0.5 mol) of 3-diethylaminopropylamine. The reaction product is mixed with 500 ml of ether, the mixture is filtered and the residue is washed with ether. After drying at 60° C. in vacuo, the crude product is recrystallised in acetone to yield 69.44 g (53.4% of theory) of a white crystalline aspartic acid derivative, the melting point of which is 154.5°–156.5° C.

Elementary analysis

| calculated | found |
| --- | --- |
| 55.37% C | 55.46% C |
| 9.29% H | 9.21% H |
| 10.76% N | 10.75% N. |

The 100 MHz-$^1$H-NMR spectrum is in agreement with the following structure:

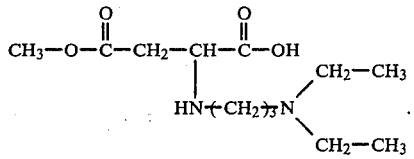

EXAMPLE 8

N-(3'-Piperidylpropyl)-aspartic acid-4-methyl ester

In a manner analogous to that described in Example 1, 28.6 g (0.2 mol+10% excess) of maleic acid-monomethyl ester, 40 ml of triethylamine and 88.4 g (0.2 mol) of N-(3'-aminopropyl)-piperidine are reacted and the reaction product is purified. The yield is 36.7 g (67.4% of theory) and the melting point of the product obtained is 172°–173° C.

Elementary analysis

| calculated | found |
| --- | --- |
| 57.06% C | 57.25% C |
| 8.91% H | 9.09% H |
| 10.24% N | 10.45% N |
| 0.48% H$_2$O | 0.48% H$_2$O. |

The 100 MHz-$^1$H-NMR spectrum is in agreement with the following structure:

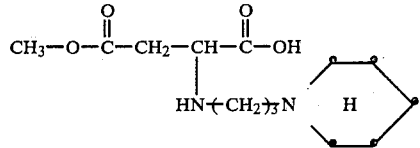

EXAMPLE 9

N-3'-(2''-Methylimidazolyl)-propyl-aspartic acid-4-benzyl ester 80 ml of triethylamine are added, in a manner analogous to that described in Example 1, to a mixture of 82.4 g (0.4 mol) of maleic acid-monobenzyl ester and 30 ml of dioxane, and the whole is subsequently reacted with 56.0 g (0.4 mol) of N-3'-aminopropyl-2-methylimidazole for 20 minutes at 83° C. The reaction mixture is then cooled to room temperature and the liquid phase is decanted; to the viscous reaction mixture are added 400 ml of diethyl ether and the mixture is stirred up. The ethereal phase is decanted; the viscous residue is dissolved in 270 ml of isopropanol at 60° C., and the solution is treated with active charcoal. The solution is filtered, the filtrate is diluted with 270 ml of diethyl ether, and the product is caused to crystallise at 0° C. The product which has crystallised out is isolated by filtration and dried at 50° C. in vacuo. There are obtained 56.3 g (40.7% of theory) of the desired aspartic acid derivative, which melts at 134° C. after recrystallisation in isopropyl alcohol.

Elementary analysis

| calculated | found |
|---|---|
| 62.59% C | 62.25% C |
| 6.71% H | 6.59% H |
| 12.17% N | 12.34% N. |

The $^{13}C$- and 100 MHz-$^1H$-NMR spectra are in agreement with the following structure:

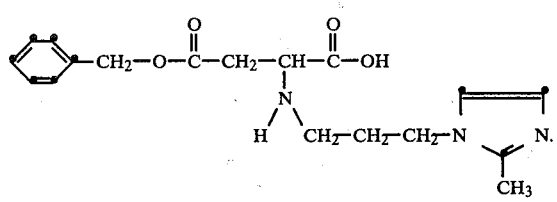

EXAMPLE 10

N-(2'-Dimethylaminoethyl)-aspartic acid-4-methyl ester 28.6 g (0.22 mol) of maleic acid-monomethyl ester, 40 ml of triethylamine and 17.6 g (0.20 mol) of 2-dimethylaminoethylamine are reacted in a manner analogous to that described in Example 1. Further processing according to Example 1 yields 14.5 g (33.2% of theory) of a crystalline aspartic acid derivative, which melts at 164° to 166°.

Elementary analysis

| calculated | found |
|---|---|
| 49.01% C | 49.05% C |
| 8.37% H | 8.14% H |
| 12.70% N | 12.69% N |
| 1.06% H$_2$O | 1.06% H$_2$O. |

The analytical data are in agreement with the following structure:

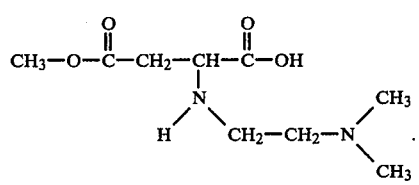

APPLICATION EXAMPLES

EXAMPLE I

Use of N-(3'-dimethylaminopropyl)-aspartic acid-4-n-butyl ester as latent accelerator in epoxide resin/dicyandiamide systems A comparative formulation is firstly produced: From a solid halogenated epoxide resin based on brominated bisphenol-A and epichlorohydrin and having an epoxide content of 1.92 equivalents/kg and a bromine content of 21 percent by weight, there is prepared a 20% solution in methyl ethyl ketone (component I).

The curing agent, dicyandiamide, is used as a 10% solution in methyl glycol (component II).

The comparative formulation consists of:

| component I | : | 62.5 | g |
|---|---|---|---|
| component II | : | 15 | g |
| methyl glycol | : | 5 | g |
| benzyldimethylamine | : | 0.1 | g, | and, after an appropriate thorough mixing, is a clear homogeneous solution (formulation A).

An analogous formulation is then produced, wherein N-(3'-dimethylaminopropyl)-aspartic acid-4-n-butyl ester is used as accelerator in this case in place of benzyldimethylamine:

| component I | 62.5 | g |
|---|---|---|
| component II | 15 | g |
| methyl glycol | 5 | g |
| N-(3'-dimethylaminopropyl)-aspartic acid-4-n-butyl ester | 0.25 | g. |

The solid aspartic acid ester is dissolved in 5 g of methyl glycol. After thorough mixing, this formulation too is a clear homogeneous solution (formulation B).

COMPARATIVE MEASUREMENTS

Measurements are made of the gelling time at 100° C. and 150° C., respectively, (on the gelling-time plate) and of the service life at 40° C. in the Höppler viscosity tube. The point of time at which a doubling of the initial viscosity is given as the end point of the service life.

| | Formulation | | |
|---|---|---|---|
| | A | B | Δ% |
| gelling time at 100° C. (sec.) | 9000 | 11,400 | |
| gelling time at 150° C. (sec.) | 660 | 560 | |
| latency factor (100°/150° C.)** | 13.6 | 20.4 | +50 |
| service life at 40° C. (hours) | 268 | 340 | +26.9 |

** = ratio of the gelling times at 100°/150°

It is clear from the comparison that with use of the N-(3'-dimethylaminopropyl)-aspartic acid ester according to the invention as curing accelerator in epoxide resin/dicyandiamide mixtures, there are obtained a shortening of the gelling time at 150° C. and a lengthening of the gelling time at 100° C., two desirable factors from the point of view of application. Furthermore, the resin/curing agent mixture containing the curing accelerator according to the invention shows an advantageous lengthening of service life at 40° C.

EXAMPLE II

Use of the N-(3'-dimethylaminopropyl)-aspartic acid-4-methyl ester as latent accelerator for a powder system based on epoxide resin and carboxylic acid anhydride The powder system consists of a solid epoxide resin based on bisphenol-A and epichlorohydrin and having an epoxide content of 1.1 equivalents/kg, trimellitic acid anhydride as curing agent and imidazole:

| | | |
|---|---|---|
| epoxide resin | 50 | g |
| trimellitic acid anhydride | 5.5 | g |
| imidazole | 0.55 | g. |

To produce the powder, the epoxide resin is preground for 16 hours in a ball mill. The other two solid components are subsequently added, and the whole is then ground for 5 hours and at the same time thoroughly mixed together.

Formulation B (according to the invention)

This is produced in a manner fully analogous to that of producing the above formulation A, and formulation B comprises:

| | | |
|---|---|---|
| epoxide resin | 50 | g |
| trimellitic acid anhydride | 5.5 | g |
| N-(3-dimethylaminopropyl)-aspartic acid-4-methyl ester | 1.375 | g. |

Comparative measurements

Measurements are taken of the gelling time at 120° and 180° C., respectively, (gelling-time plate), and of the storage stability at 40° C. The last-mentioned is assessed by further measuring the gelling time at 180° C. after a storage-time of 30 days. In the case of a powder system in practice, there must be no significant change in reactivity after this length of time. The powder system must also remain fully satisfactorily flowable.

| | Formulation | | |
|---|---|---|---|
| | A | B | Δ % |
| Gelling time at 120° C. (sec.): | 315 | 1485 | |
| gelling time at 180° C. (sec.) | 70 | 70 | |
| latency factor (120°/180° C.)* | 4.5 | 21.2 | +371% |
| gelling time at 180° C. after 30 days' storage at 40° C. | 40 | 70 | |
| flowability after 30 days' storage at 40° C. | good | good | |

\* = ratio of the gelling times at 120°/180° C.

Whereas both powder systems have identical gelling times at 180° C., the formulation B, which contains as accelerator an aspartic acid ester according to the invention instead of imidazole, has at 120° C. a gelling time almost 5 times longer than that of formulation A at 120° C. This means that with formulation B there is obtained a considerably higher latency factor, a result which is desired on application, for example as powder lacquer, because there is thus obtained a greater level of certainty in the extrusion process. In addition, the formulation B has a storage stability at 40° C. which is incomparably better than that of the comparative formulation A at 40° C.

What is claimed is:

1. An N-substituted aspartic acid monoester of the formula

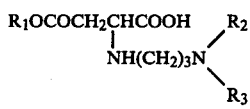

wherein
$R_1$ is alkyl having 1 to 4 C atoms or cyclohexyl, and $R_2$ and $R_3$ are each a methyl or ethyl group, or together with the N atom they form an N-heterocyclic ring of the formula

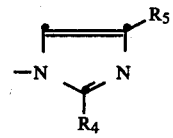

wherein $R_4$ is methyl, and $R_5$ is a hydrogen atom or ethyl.

2. N-(3'-Dimethylaminopropyl)-aspartic acid-4-methyl ester as compound according to claim 1.

3. N-(3'-Dimethylaminopropyl)-aspartic acid-4-n-butyl ester as compound according to claim 1.

4. N-(3'-Dimethylaminopropyl)-aspartic acid-4-isopropyl ester as compound according to claim 1.

5. N-(3'-Methylethylaminopropyl)-aspartic acid-4-cyclohexyl ester as compound according to claim 1.

6. N-(3'-Diethylaminopropyl)-aspartic acid-4-methyl ester as compound according to claim 1.

* * * * *